(12) United States Patent
Gagliardoni et al.

(10) Patent No.: US 8,551,057 B2
(45) Date of Patent: Oct. 8, 2013

(54) PINCH CLAMP ASSEMBLY

(75) Inventors: Giancarlo Gagliardoni, Estado Miranda (VE); Giuseppe Antonio Nichetti, Pandino (IT)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/379,203

(22) PCT Filed: Aug. 14, 2009

(86) PCT No.: PCT/EP2009/060556
§ 371 (c)(1),
(2), (4) Date: Dec. 19, 2011

(87) PCT Pub. No.: WO2010/149231
PCT Pub. Date: Dec. 29, 2010

(65) Prior Publication Data
US 2012/0101438 A1 Apr. 26, 2012

(30) Foreign Application Priority Data

Jun. 25, 2009 (WO) .................. PCT/EP2009/004601

(51) Int. Cl.
*A61M 5/175* (2006.01)
*A61M 5/142* (2006.01)
*F04B 43/08* (2006.01)

(52) U.S. Cl.
USPC ......... 604/250; 604/151; 604/153; 417/477.2

(58) Field of Classification Search
USPC ............ 417/477.2; 251/10; 604/34, 250, 131, 604/151, 153
See application file for complete search history.

(56) References Cited

U.S. PATENT DOCUMENTS

| | | |
|---|---|---|
| 4,689,043 A | 8/1987 | Bisha |
| 4,944,485 A | 7/1990 | Daoud et al. |

(Continued)

FOREIGN PATENT DOCUMENTS

| | | |
|---|---|---|
| JP | 2007236618 | 9/2007 |
| TW | 1227148 | 10/2002 |

(Continued)

OTHER PUBLICATIONS

PCT International Search Report for Application No. PCT/EP2009/060556 mailed on Aug. 14, 2010.

*Primary Examiner* — Nicholas Lucchesi
*Assistant Examiner* — Benjamin Koo
(74) *Attorney, Agent, or Firm* — K&L Gates LLP

(57) ABSTRACT

A pinch clamp assembly for engaging a tube with an enteral feeding or infusion pump adapted to feed nutritionals or to infuse medical solutions to a patient, is provided comprising a base (1) comprising holding means (3) for holding a pumping section (10) of the tube in operative engagement with the base (1) and supporting means (5) for supporting a connector (6), a clamping element (7) having clamping surfaces engageable with the pumping section (10) and moveable between an open position allowing flow of fluid through the pumping section (10) and a closed position wherein the pumping section (10) is occluded by the clamping element (7), and locking means adapted to engage with each other in the closed position and adapted to interact with releasing means external to the pinch clamp assembly so as to bring the clamping element (7) from the closed to the open position, a connector (6) for connecting the tube with a port on a patient, the connector (6) being removable from the pinch clamp assembly, the clamping element (7) further comprising a retaining lever (16), wherein in the open position of the clamping element (7) the connector (6) is retained by the retaining lever (16), and wherein the clamping element (7) is adapted to engage with the releasing means (43) to release the clamping element (7) to the open position when the pinch clamp assembly is mounted to the enteral feeding or infusion pump and the connector (6) is removed.

14 Claims, 8 Drawing Sheets

(56) References Cited

U.S. PATENT DOCUMENTS

| | | |
|---|---|---|
| 5,401,256 A | 3/1995 | Stone et al. |
| 5,954,485 A | 9/1999 | Johnson et al. |
| 2007/0265559 A1 | 11/2007 | Kunishige et al. |

FOREIGN PATENT DOCUMENTS

| | | |
|---|---|---|
| WO | 9630679 | 10/1996 |
| WO | 03011377 | 2/2003 |

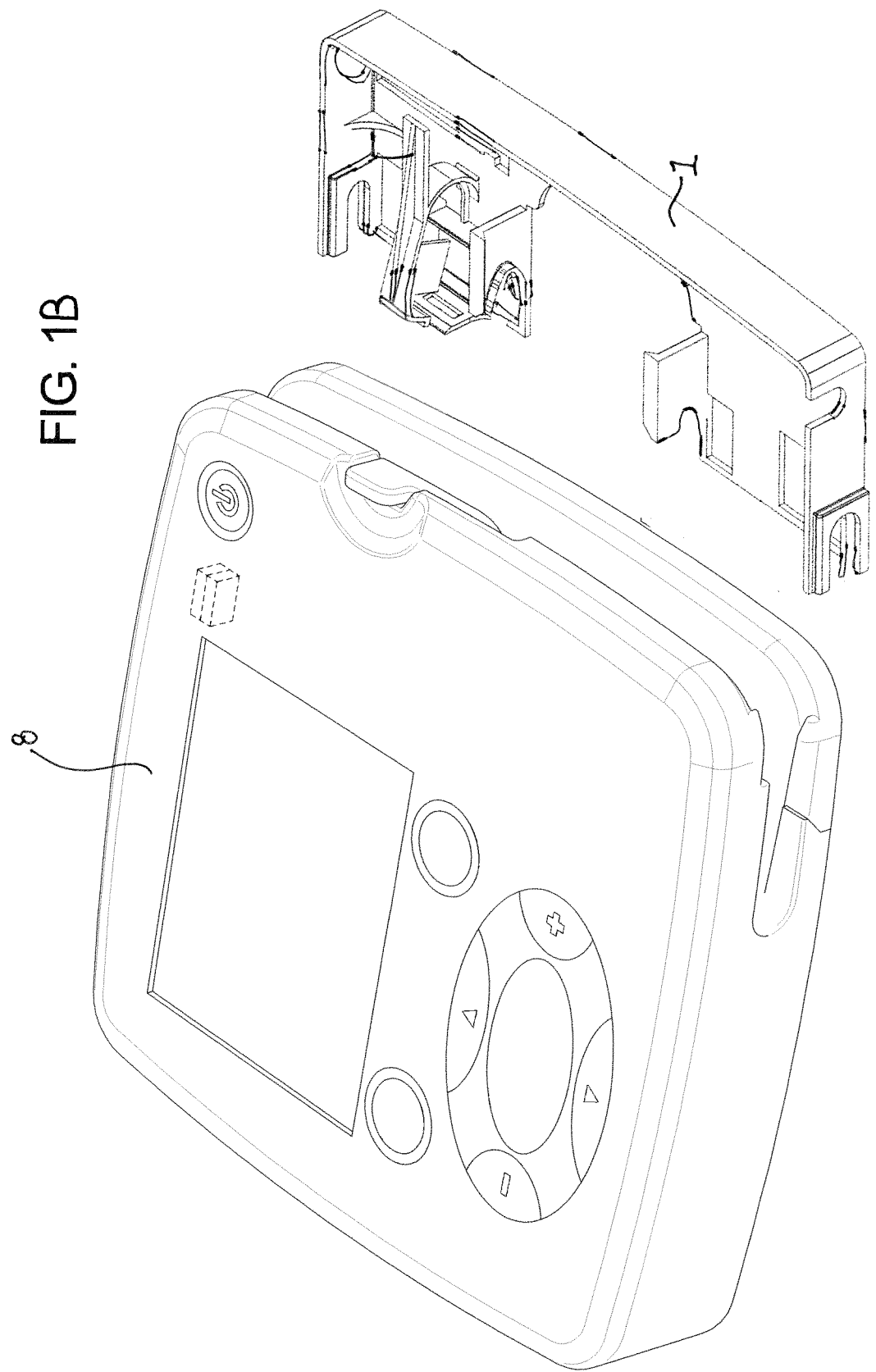

PINCH CLAMP ASSEMBLY

CROSS REFERENCE TO RELATED APPLICATIONS

The present application is a National Stage of International Application No. PCT/EP2009/060556, filed on Aug. 14, 2009, which claims priority to International Application No. PCT/EP2009/004601, filed on Jun. 25, 2009, the entire contents of which are being incorporated herein by reference.

BACKGROUND OF THE INVENTION

The present invention relates to a pinch clamp assembly for engaging a tube with an enteral feeding pump adapted to feed nutritionals or an infusion pump adapted or to infuse medical solutions to a patient. More particularly, the present invention relates to a pinch clamp assembly in the form of a cassette with a clamping element for use on enteral feeding sets or infusion sets and the like, wherein the clamping element prevents the free-flow of enteral formula through the enteral feeding set or of solutions through the infusion set unless the cassette and the clamping element are properly mounted in a housing or some other structure of an enteral feeding pump or infusion pump.

The use of infusion and feeding sets to administer solutions and food to a patient is well known in medical arts. Infusion and enteral sets are used for both enteral and parenteral application, respectively. For hygienic reasons the infusion and enteral sets must be disposed of immediately after use, making it single-use equipment which may be recycled afterwards. Enteral feeding pumps are used to provide the patient with nutrition and medication (formula) when they are unable, for a variety of reason, to eat normally. Parenteral (intravenous) solutions are provided to patients to ensure adequate hydration and to provide needed nutrients, minerals and medication. Often, the enteral or infusion set is placed in a free standing arrangement in which gravity forces the formula or solution into the patient. The rate at which the solution enters the patient can be roughly controlled by various clamps, such as roller clamps, which are currently available on the market.

In many applications, it is necessary to precisely control the amount of solution or formula which enters the patient. When this is the case, a regulating device such as an infusion pump, is placed along the infusion set to control the rate at which the solution is fed to the patient. In application where a pump etc. is used the clamps used to regulate flow are typically open to their fullest extent to prevent the clamp from interfering with the proper functioning of the pump. The clamp is opened with the expectation that the enteral feeding pump or infusion will control fluid flow through the enteral or infusion set. However, emergencies or other distractions may prevent the medical personnel from properly loading the enteral or infusion sets in the enteral feeding pump or the infusion pump. Furthermore, the enteral or infusion sets may be inadvertently dislodged from the pump during operation of the pump.

When the enteral or infusion set is not properly loaded in the pump and the clamp has been opened, a situation known as free-flow often develops. The force of gravity causes the solution or the formula to flow freely into the patient unchecked by the pump or other regulating device. Under a free-flow condition, an amount of solution or formula many times the desired dose can be supplied to the patient within a relatively short time period. This can be particularly dangerous if the solution contains potent medicine or the patient's body is not physically strong enough to adjust to the large inflow of solution or formula. Thus there is a need for a device that prevents a free-flow condition if the enteral or infusion set is not properly mounted in the pump or other regulation means. It is furthermore important that the device is tamper-resistant with regard to the generation of the free-flow condition. Another requirement for such enteral feeding or infusion sets is a long storage period which may be up to several years. Therefore a sticking and continuous deformation of the silicon tube is to be avoided which may result in a deviation of its regular flow properties when using it.

Several approaches have been taken to avoid the above mentioned free-flow situation one of which is disclosed in WO 96/030679 A1. Therein, a pinch clip occluder utilizes a clamping mechanism with at least one arm nested at least partially within a housing which serves as an adjustment mechanism by moving the arm between a position in which the arm occludes flow through an infusion set, and a position in which it allows free-flow through the infusion set. One problem related therewith is that the pinch clip occluder can still be manipulated in a way that the spring force may be countered by other external elements such as a squeeze, a fastener or the like. Furthermore, the metal spring inside the pinch clip occluder according to WO 96/030679 A1 is not made of plastic material thus preventing the possibility of being recycled together with the other plastic components. This makes the recycling process of the infusion set more tedious and thus more expensive. Another disadvantage of said infusion set including the pinch clip occluder is that mounting it to the infusion or enteral feeding pump is rather complicated, i.e. the silicon tube has to be positioned exactly in the recesses formed therefore and wrapped around the rotor unit etc. In addition, a major drawback of this known pinch clip occluder is that when the cap with the prone is left inside the pinch clip occluder to open the tube, a free-flow situation is caused even when the infusion set is not attached to the pump.

U.S. Pat. No. 4,689,043 describes an IV tube activator for use with a peristaltic IV infusion pump comprising means that require the closure of a tube associated clamp upon engagement of the IV tube with the pump and upon any subsequent disengagement of the IV tube from the pump. This IV tube activator also represents a rather complicated structure and will not solve the problem of storage of the clamped silicon tube before using it in the infusion pump. Furthermore, setting up the infusion set with the IV tube activator is cumbersome and error-prone due to the many different components.

SUMMARY OF THE INVENTION

It is therefore the object of the present invention to provide a pinch clamp assembly for engaging a tube with an enteral feeding or infusion pump adapted to feed nutritionals or to infuse medical solutions to a patient, which comprises a relatively simple construction, ensures an anti-free-flow mechanism that works at all times, allows for a long time storage of the silicon tube, is uniform with regard to the used material in order to be easily recyclable and can be used with a number of enteral feeding or infusion pumps.

This object is solved by the features of claim 1. Advantageous embodiments of the invention are subject of the subclaims.

According to the invention, a pinch clamp assembly for engaging a tube with an enteral feeding or infusion pump adapted to feed nutritionals or to infuse medical solutions to a patient is provided with the following components: a base comprising holding means for holding a pumping section of the tube in operative engagement with the base and supporting means for supporting a connector, a clamping element having clamping surfaces engageable with the pumping section and moveable between an open position allowing flow of fluid through the pumping section and a closed position wherein the pumping section is occluded by the clamping element, and locking means adapted to engage with each other in the closed position and adapted to interact with releasing means external to the pinch clamp assembly so as to bring the clamping element from the closed to the open position, a connector for connecting the tube with a port on a patient, the connector being removable from the pinch clamp assembly. It comprises the features that the clamping element further comprises a retaining lever, wherein in the open position of the clamping element the connector is retained by the retaining lever, and wherein the clamping element is adapted to engage with the releasing means to release the clamping element to the open position when the pinch clamp assembly is mounted to the enteral feeding or infusion pump and the connector is removed.

Thereby, the free-flow condition is prevented when the pinch clamp assembly is in its delivery state because the connector which is to be connected to the port of the patient is still part of the pinch clamp assembly and cannot be removed unless the clamping element is in its closed position. Before a user is able to remove connector from the assembly, the clamping element must be brought into its closed position preventing any flow through the pumping section of the silicon tube. Therefore, the free-flow condition is again prevented when the respective connectors are connected to the port on the one end and to the solution or formula container on the other end. In this state, i.e. after closing the clamping element and the removal of the connector, the pinch clamp assembly may be inserted into the enteral feeding or infusion pump. When inserting the pump, the clamping element is opened due to the interaction of the releasing elements with the clamping element. However, there is no free-flow condition because the pumping section of the silicon tube is so tightly wrapped around the pumping mechanism (rotor unit) of the enteral feeding or infusion pump that a flow of solution through the silicon tube is prevented. Thus, a free-flow condition of an infusion set comprising the pinch clamp assembly according to the present invention is avoided at all times, in particular before its first use.

Other advantages of the pinch clamp assembly according to the invention are that the assembly may be stored for a long time such as five years in its delivery state because the clamping element is in its open position and the silicon tube is not compressed or pinched thus preventing degradation or sticking of the material. Also the anti-free-flow mechanism is an integral part of the pinch clamp assembly avoiding any additional components.

It is to be noted that to bring the pinch clamp assembly into the delivery state, which is usually as an entire infusion or enteral feeding set wrapped in single poly pouch or blister package, the single components of the pinch clamp assembly have to be put together accordingly, thereby bringing the clamping element into its closed position and thus occluding the silicon tube. However, the period of time where the flow is occluded is only minimal because the releasing means are immediately applied to the locking means of the clamping element thereby releasing it to its open position.

The pinch clamp assembly of the present invention is also tamper-resistant because for a normal user it is impossible to open the clamping element with her or his hands when the clamping element is pushed down to its closed position and the connector is removed. Only the intention to tamper with the assembly using suitable tools (which are usually not available to the medical personnel setting up enteral feeding or infusion sets) will open the clamping element and involves the risk of destroying the function of the whole assembly.

Preferably the base and the clamping element are integrally formed. This enables a compact pinch clamp assembly and reduces the number of parts involved in fabrication.

In an advantageous embodiment the connector is an enteral spike, an IV (intravenous) spike, an enteral feeding adapter, an IV luer lock adapter or other enteral or IV component. All possible connectors known in the art of enteral feeding or infusion can be used.

In a preferred embodiment the base is formed as a cassette such that the pinch clamp assembly may be integrally mounted to the enteral feeding or infusion pump. A cassette provides a flat construction which is not bulky and yet comprises a compact format.

In a preferred embodiment the pinch clamp assembly is made of recyclable plastic material such as thermoplastics, and the pumping section of the tube is made of silicon or silicon replacement tubing. This enables a simple recycling procedure of this one-way and single-use equipment and avoids tedious sorting procedures.

In an advantageous embodiment the clamping element comprises a first leg with a tube blocking portion, a second leg with a flat surface, a bending portion acting as a spring element, first locking means at the free end of the first leg and second locking means at the free end of the second leg and the retaining lever is adjacent to the first leg and the bending portion, wherein the tube blocking portion and the flat surface may be pressed upon one another to squeeze the tube therebetween, and wherein the first and second locking means are engageable with each other in the open position or in the closed position.

In a preferred embodiment the clamping surfaces are uneven, corrugated or finned. Depending on the specific requirements of the silicon tubing, different set-ups of the clamping surfaces may be used. It is also possible to change the function of the first leg and the second leg.

Preferably in the open position of the clamping element the retaining lever exerts a force on the connector so that the connector cannot be removed from the pinch clamp assembly. With preference the connector is removable from the pinch clamp assembly only when the clamping element is in the closed position. This avoids the free-flow condition when medical personnel is applying an infusion set or enteral feeding set comprising the pinch clamp assembly according to the invention to an infusion or enteral feeding pump.

Preferably the supporting means comprise a first recess for accommodating the connector and a second recess for accommodating the tube associated with the connector. In this way, the connector and the tube associated with it can be held tight within the assembly (or cassette). This enables a tidy and compact design of the assembly which makes the use of the infusion set easier for medical personnel.

According to another embodiment of the present invention an enteral feeding or infusion pump comprises a pinch clamp assembly as mentioned above, wherein the pump comprises releasing means adapted to engage with the clamping element so as to release the clamping element from the closed to the open position.

Preferably the flow through the pumping section is only enabled when the pinch clamp assembly is mounted. This ensures that the anti-free-flow mechanism is only disabled when the pinch clamp assembly is entirely mounted to the infusion pump.

BRIEF DESCRIPTION OF THE DRAWINGS

The above object, features and advantages of the present invention will become apparent from a consideration of the following detailed description presented in connection with the accompanying drawings in which:

FIG. 1B shows a perspective view of a pump and a cassette according to a preferred embodiment of the pinch clamp assembly according to the invention.

DETAILED DESCRIPTION

Figure 1A:
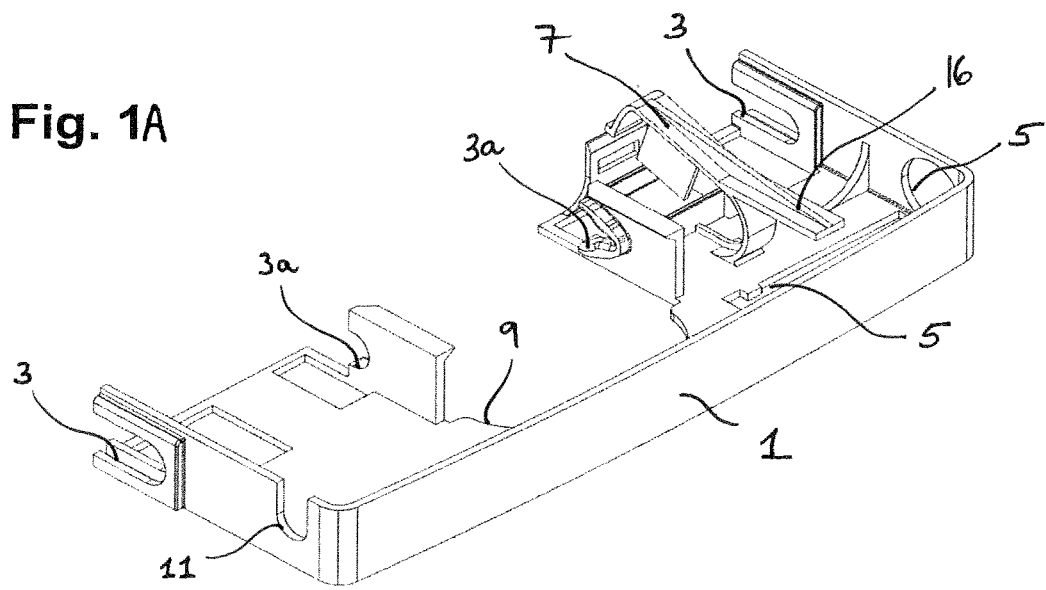
FIG. 1A shows a perspective view of a cassette according to a preferred embodiment of the pinch clamp assembly according to the invention.

FIG. 1A depicts a perspective view of the main component of a preferred embodiment of the pinch clamp assembly according to the invention which is comprised of cassette 1 forming the base of the assembly. Cassette 1 is configured generally rectangular and in a relatively flat structure. Cassette 1 comprises holding means 3 at opposing sides to support the pumping section of a silicon tube (not shown in this figure). Further holding means 3a to accommodate the silicon tube are positioned towards the center and near the longitudinal edge of the cassette 1. Supporting means 5 are provided in cassette 1 in the form of a substantially round recess formed in a side wall of the cassette 1 and a further substantially rectangular recess formed in the ground plate of cassette 1. Supporting means 5 are provided to support a connector which will be described in more detail later. The central element of the pinch clamp assembly according to the invention is clamping element 7 which in the shown preferred embodiment is integral with cassette 1. The details of clamping element 7 will be described with reference to FIG. 2D and FIG. 2E. In the side wall opposing supporting means 5 there is provided a tube recess 11 for supporting the tube associated with the connector. In order not to over-complicate the figures with components not essential for the invention, the tube has been omitted at this point. The bottom portion of cassette 1 comprises a rotor unit recess 9 which is substantially in the shape of a rectangle with its inner corners rounded. When mounting the pinch clamp assembly according to the invention to the enteral feeding or infusion pump 8 the pins of the peristaltic rotor unit will fit into the space freed by the rotor unit recess 9. A schematic representation of a pump (e.g., an enteral feeding or infusion) that may be used with the present cassettes 1 is provided in FIG. 1B. Holding means 3a are formed on parallel side walls which are located at the edge of recess 9 and substantially rectangular to the direction of the tube in order to stabilize said mounting procedure.

Figure 2A:
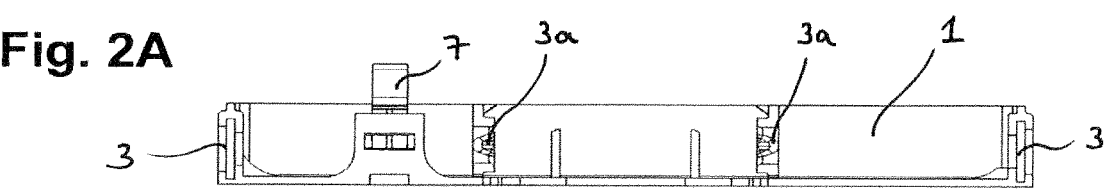
FIGS. 2A, 2B, 2C show a front view, plan view, and rear view, respectively, of the cassette shown in FIG. 1.
Figure 2B:
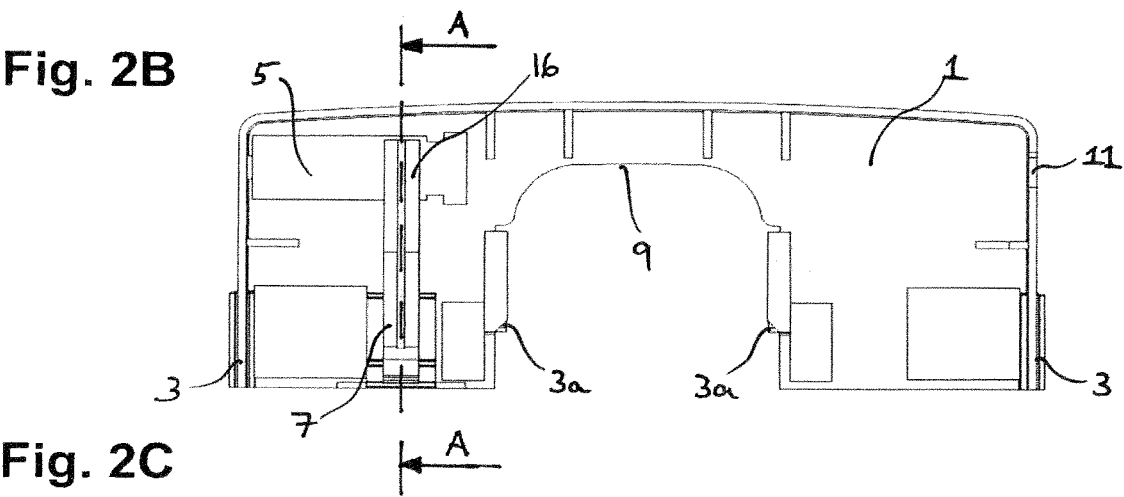
Figure 2C:
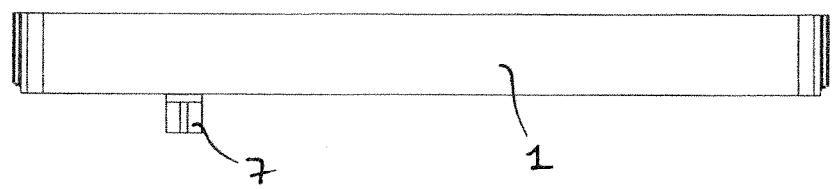

FIGS. 2A, 2B and 2C are front, plan and rear views of the pinch clamp assembly components of FIG. 1, wherein like numerals refer to like elements.

Figure 2D:
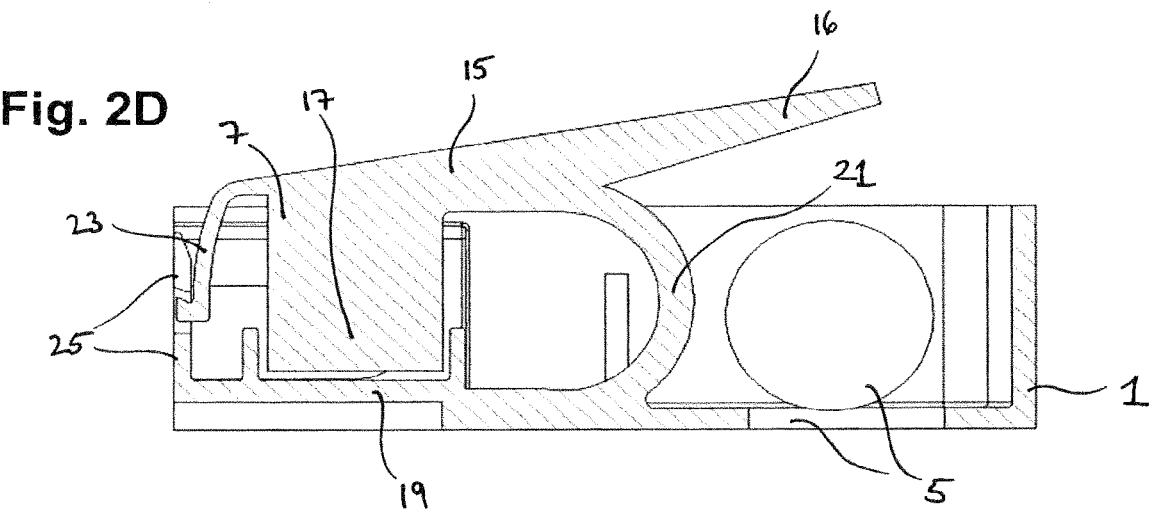
FIGS. 2D, 2E show section views on the line A-A of FIG. 2B, wherein the clamping element is in the closed and open position, respectively.
Figure 2E:
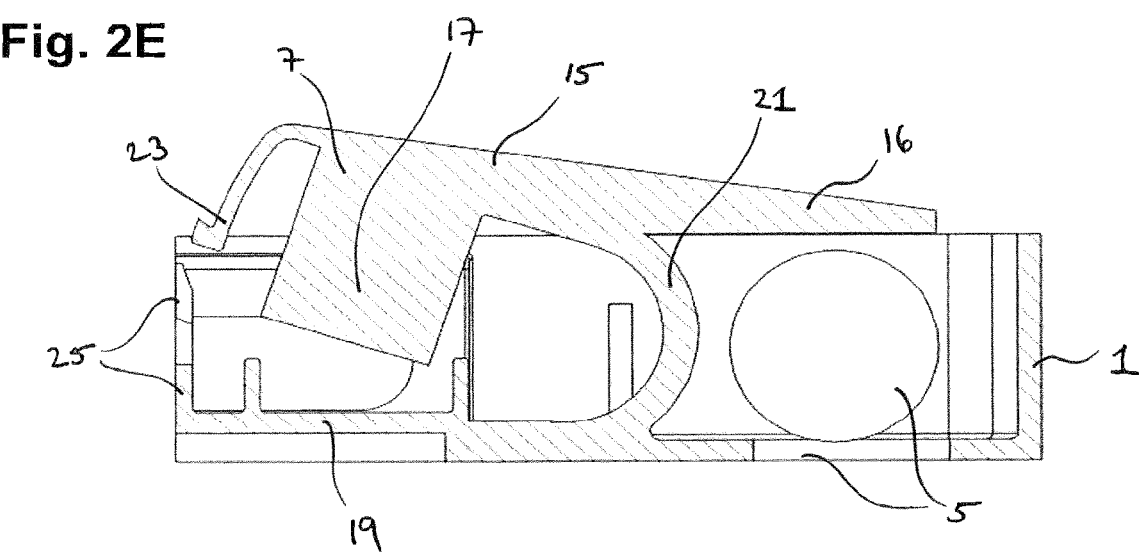

FIGS. 2D and 2E show an enlarged and sectional side view of the cassette 1 according to FIG. 1 wherein the clamping element 7 is in the closed (FIG. 2D) and the open position (FIG. 2E). Clamping element 7 generally comprises a first leg 15 with a tube blocking portion 17 in the form of a substantially rectangular plate which is attached to the first leg 15 at a substantially right angle. On the far end with respect to the tube blocking portion 17 first leg 15 comprises a retaining lever 16. In the shown embodiment the second leg 19 of clamping element 7 is integrally formed with the mount plate of cassette 1. The linking element between first leg 15 and second leg 19 of clamping element 7 is bending portion 21 which acts as a spring element so that clamping element 7 may be moved from a tension-less open position to a closed position. The retaining lever 16 is formed at the transition area between first leg 15 and bending portion 21 and extends at least partially into the space above the round supporting means 5, preferably at an angle of between 5° and 30°. In order to stabilize the lever function of retaining lever 16 a T-bar like protrusion is formed on the upper surface of first leg 15 and retaining lever 16, as can best be seen in FIG. 1.

At the free end of first leg 15 there is provided a first locking means 23 which extends in a substantially right angle towards the ground plate of cassette 1. The T-bar like protrusion extends substantially from the near end of first locking means 23 to the far end of retaining lever 16. First locking means 23 comprises a protrusion extending generally away from bending portion 21. The counterpart of first locking means 23 is second locking means 25 located at the free end of second leg 19. In the preferred embodiment of the present invention, second locking means 25 comprise a horizontal slit with a length such that an engagement of the hook-like first locking means 23 and the slit of second locking means 25 in a closed position of clamping element 7 is enabled (shown in FIG. 2D). Thus second locking means 25 are in this embodiment wider than the first locking means 23, as can be seen in FIG. 2A. In the preferred embodiment in the open position of clamping element 7 there is no engagement between the first and second locking means (shown in FIG. 2E). It is to be noted that any other engaging elements may be used for first and second locking means 23, 25 in order to ensure the locking function of clamping element 7.

Moving clamping element 7 from the open position to the closed position is simple: by pressing on the upper surface of first leg 15 first locking means 23 is brought further down and will eventually engage at its hook-like protrusion with the slit formed in second locking means 25 against the spring force of bending portion 21 which results in a stable closed condition of clamping element 7. By briefly disengaging first locking means 23 and second locking means 25 clamping element 7 can be brought from the closed to the open position. This may be accomplished by bending second locking means 25 away from first locking means 23 into the direction away from bending portion 21, i.e. substantially parallel to the plane of second leg 19. Alternatively, one could press against first locking means 23 through the slit of second locking means 25 substantially parallel to the plane of second leg 19. Since access from the outside onto second locking means 25 is occluded by first locking means 23 particular tools, or release members 4, have to be used to facilitate the releasing of the engagement of first and second locking means 23, 25 such as a very small pin or screw driver.

It is to be noted, that other types of locking means may be used for clamping element 7 such as the mechanism used in a cable strap/tie wrap, magnetic closure mechanism or Velcro lock. In alternative embodiments (not shown) two or more hook-like protrusions of first locking means 23 which are adapted to engage with a corresponding plurality of slits on second locking means 25 could be used. Then, special tools adapted to disengage the locking means will have to be used.

As can be seen from FIGS. 2D and 2E, the tube locking portion 17 will, in the closed position, almost touch the inner surface of the second leg 19 thereby squeezing the pumping section of silicon tube (not shown) in order to occlude the flow therethrough. In the shown embodiment the clamping surfaces of the tube blocking portion 17 and the second leg 19 are even. However, it is possible that the clamping surfaces are uneven, corrugated or finned so as to facilitate the squeezing function of the clamping element 7 depending on the characteristics of the silicon tube.

Figure 3A:
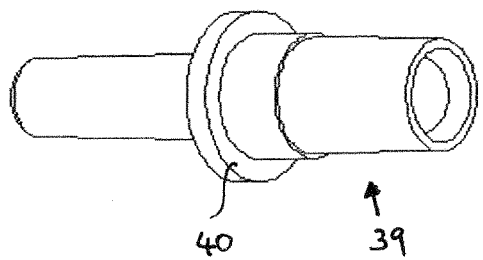
FIGS. 3A, 3B show perspective views of a tube fitting element for a preferred embodiment of the pinch clamp assembly according to the invention.
Figure 3B:
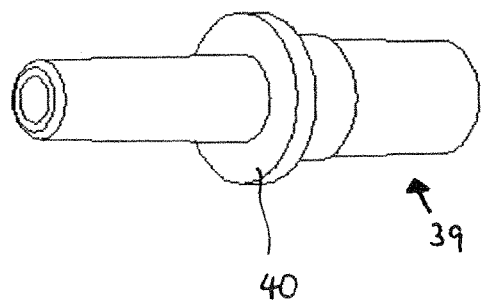

FIGS. 3A and 3B show perspective views of a tube-fitting element 39 which is adapted to hold the pumping section of the silicon tube and to fit into the holding means 3 provided in the cassette 1 of the pinch clamp assembly (see FIG. 1). In order to provide a good fit the tube fitting elements comprise a flange 40 which is adapted to engage the recesses formed in the holding means 3 of cassette 1.

Figure 4:
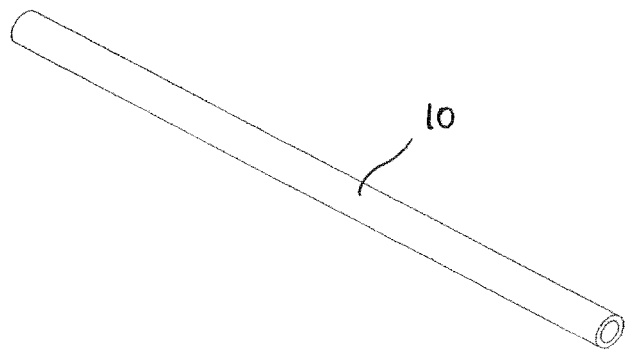
FIG. 4 shows a silicon tube of the preferred embodiment of the pinch clamp assembly according to the invention.

FIG. 4 shows the pumping section or silicon tube 10 which is arranged in the pinch clamp assembly according to the invention between the clamping surfaces of first leg 15 and second leg 19 and which is on either end tightly arranged at the respective ends of tube fitting elements 39. It is to be noted, that usually only the pumping section of the tubing portion of the entire infusion set is made of silicon, whereas the remaining portions of the tube are made of PVC (polyvinylchloride)

Figure 5:
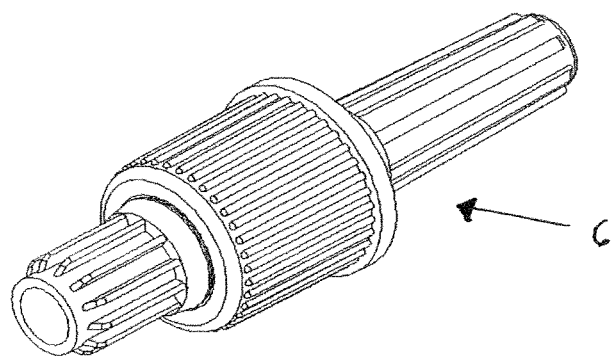
FIG. 5 shows a perspective view of an enteral universal spike with cover as part of the preferred embodiment of the pinch clamp assembly according to the invention.
Figure 6:
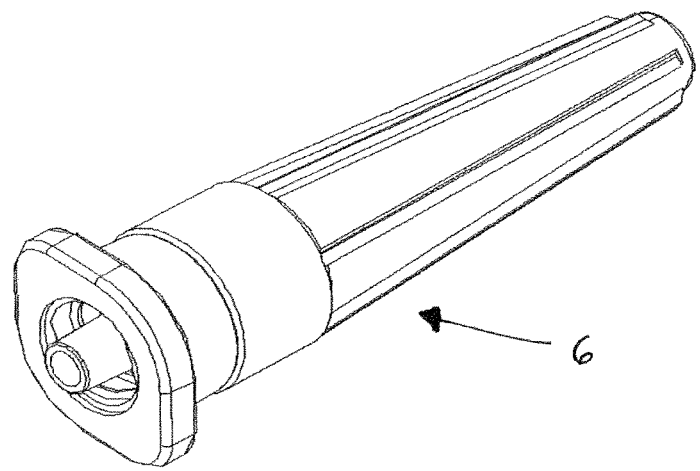
FIG. 6 shows an enteral adapter with cover of a further embodiment of the pinch clamp assembly according to the invention.

FIGS. 5 and 6 show two preferred embodiments of a connector 6 as part of the pinch clamp assembly according to the invention. The embodiment of FIG. 5 shows a universal spike which may be used in a number of enteral feeding setups, the embodiment of FIG. 6 shows an enteral adapter which on one end comprises a female luer lock or a tapered fit. It is to be noted that in FIG. 5 the universal spike is on its shorter end directly connected to a tube, e.g. via solvent bonding.

The function of the pinch clamp assembly according to the present invention will now be described in more detail with reference to FIGS. 7, 8, 9A, 9B, 10A and 10B.

Figure 7:
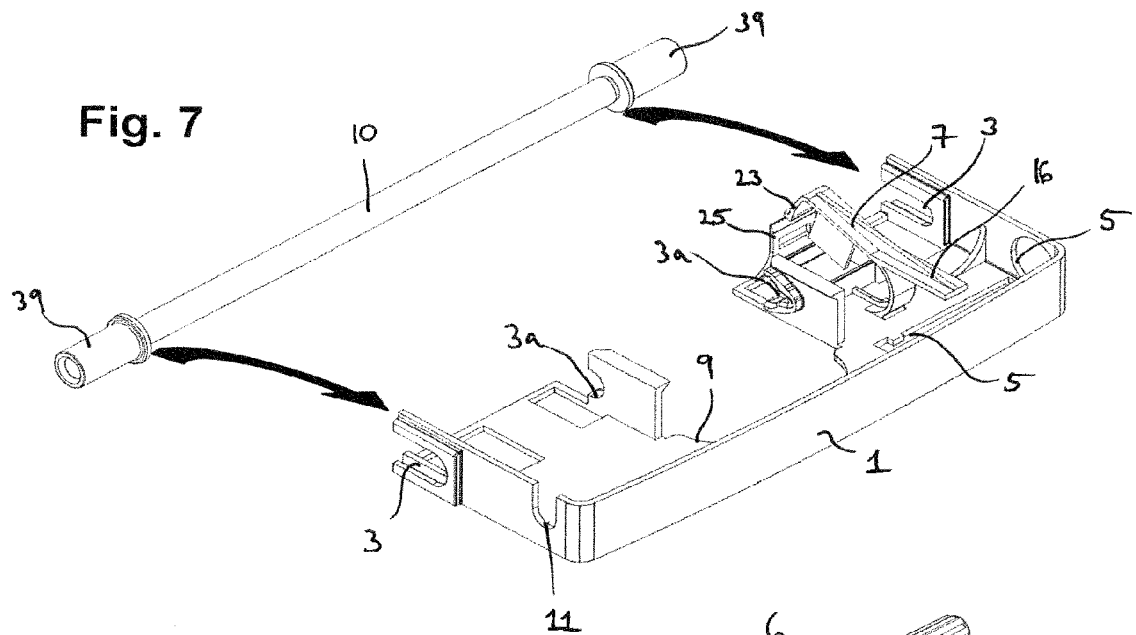
FIG. 7 shows a perspective view of the preferred embodiment of the pinch clamp assembly according to the invention in a first mounting status.

FIG. 7 shows in perspective view the first step when assembling the preferred embodiment of the pinch clamp assembly according to the invention. It is assumed that the cassette 1 is fabricated by injection moulding out of a thermoplastic material such as polypropylene, polystyrene, polyethylene or acrylnitril-butadien-styrene (ABS), also other suitable thermo-plastics may be used. The pumping section 10 of the silicon tube has already been associated with the two tube-fitting elements 39 and is now put into cassette 1. Before engaging the tube-fitting elements 39 into the holding means 3 and 3a of the cassette 1 the silicon tube 10 must be arranged between the clamping surfaces of first leg 15 and second leg 19 of clamping element 7. For this purpose, the first locking means 23 and the second locking means 25 are disengaged and first leg 15 may be widely opened to receive silicon tube 10. Alternatively, the clamping element 7 can be kept in its normal open position and the silicon tube 10 may be slid between the clamping surfaces of the clamping element 7, and then associated with tube fitting element 39 which is then engaged with holding means 3 and 3a. In the status after inserting silicon tube 10 into cassette 1 the pumping section is obviously not occluded. However, it is to be noted, that this status is merely an intermediate status while assembling the pinch clamp assembly of the invention.

Figure 8:
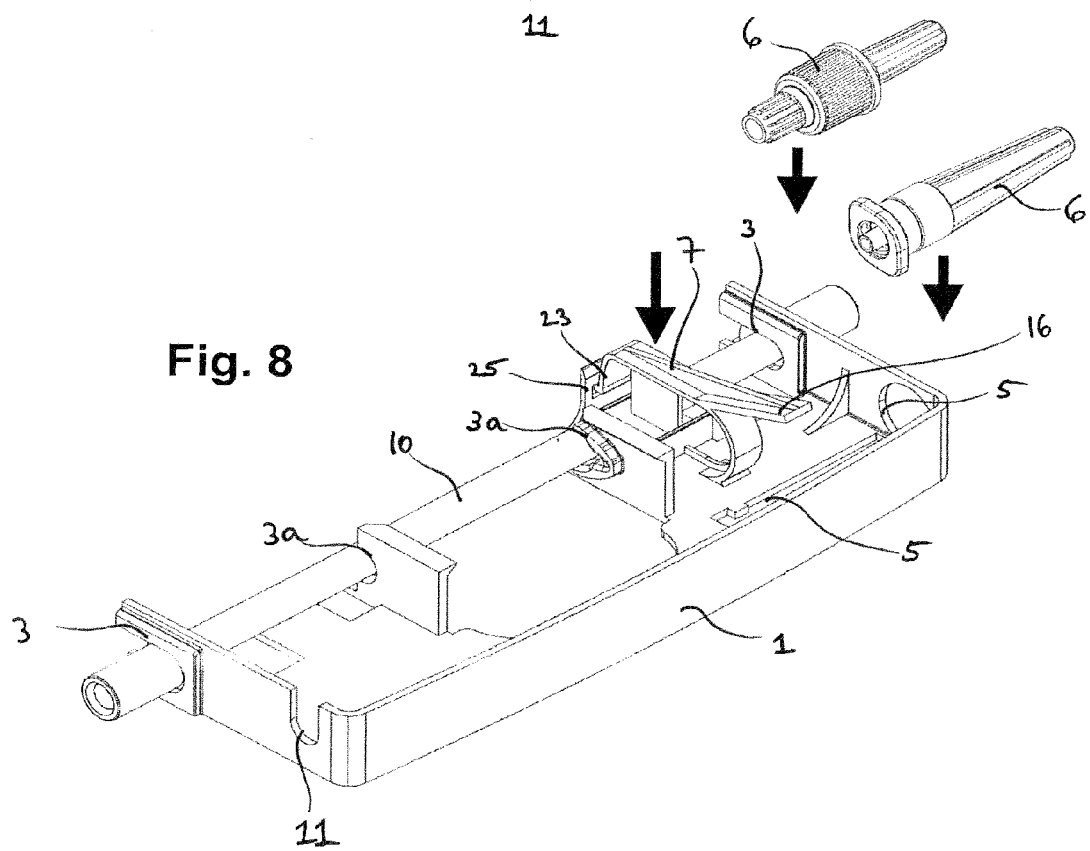
FIG. 8 shows a perspective view of a preferred embodiment of the pinch clamp assembly according to the invention in a second mounting status.

FIG. 8 shows the next step of the assembly wherein the connector 6 is embodied in two different forms, the universal spike of FIG. 5 and the enteral adapter of FIG. 6. The three arrows shall indicate the active movement with regard to the different elements of the pinch clamp assembly: firstly, the clamping element 7 is brought into the closed position by pressing on the outer surface of the first leg 15, preferably substantially above the tube blocking portion 17, thereby occluding the pumping section of the silicon tube 10. The second movement is indicative for positioning the connector 6 within the supporting means 5 of cassette 1. It must be noted that in the shown embodiment it is hardly possible to mount the connector 6 in the supporting means 5 of cassette 1 while the clamping element 7 is in the open position. This is due to the obstruction of retaining lever 16 which in the open position of clamping element 7 extends substantially parallel to the ground plane of cassette 1. However, according to the invention this obstructing function for mounting the connector 6 in the supporting means 5 of cassette 1 is not essential as will be explained later.

The status depicted in FIG. 8 is, again, an intermediate status during the assembly of the pinch clamp assembly according to the invention. It is necessary for the next step of the assembly which is mounting the connector 6 onto existing components of the pinch clamp assembly by fitting it into supporting means 5 while clamping element 7 is in closed position. It is to be noted that although two embodiments of connector 6 are shown in FIG. 8 only one connector 6 can be engaged with supporting means 5. The engagement of the connector 6 with the supporting means 5 is such that a lateral movement of connector 6 along its axis is impossible.

Figure 9A:
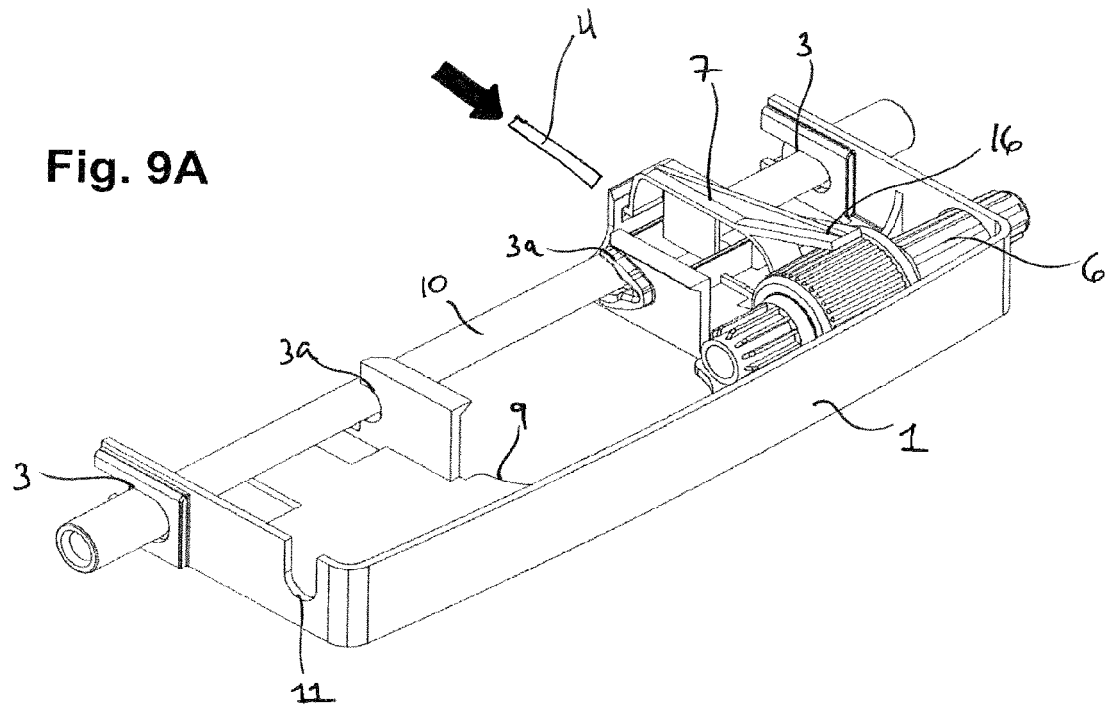
FIGS. 9A, 9B show perspective views of two preferred embodiments of the pinch clamp assembly according to the invention in a third mounting status.
Figure 9B:
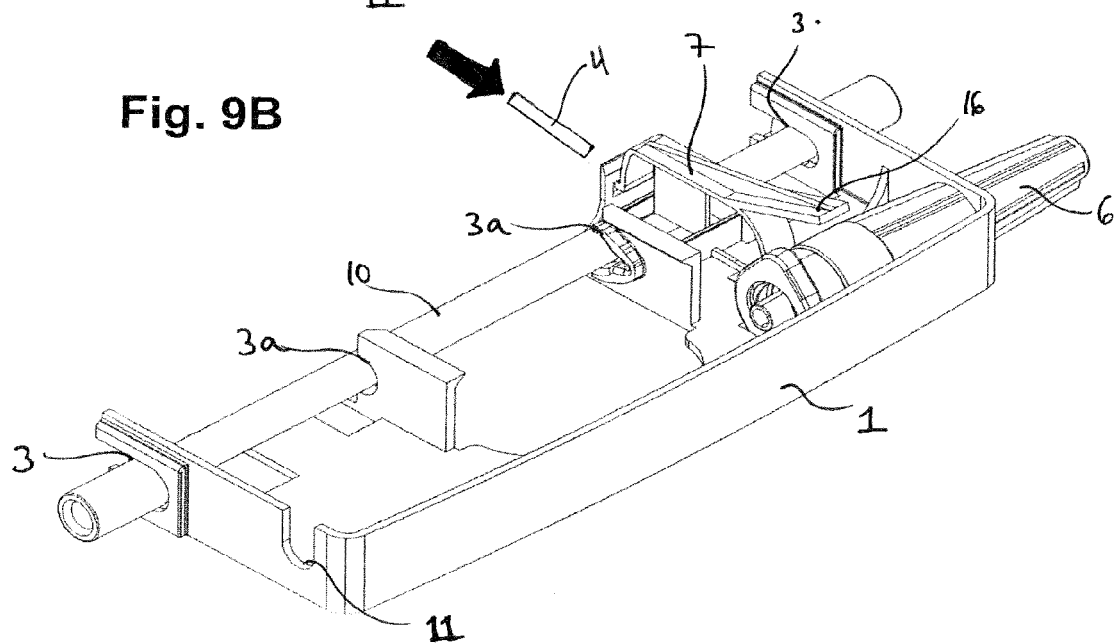

FIGS. 9A and 9B show perspective views of two preferred embodiments of the pinch clamp assembly according to the invention in the next status, after the connector 6 has been mounted onto the assembly, as explained above. In this intermediate status the clamping element 7 is holding down the pumping section 10 of the silicon tube. Furthermore, there is some free space between the upper surface of the connector 6 and the lower surface of retaining lever 16 of clamping element 7.

Figure 10A:
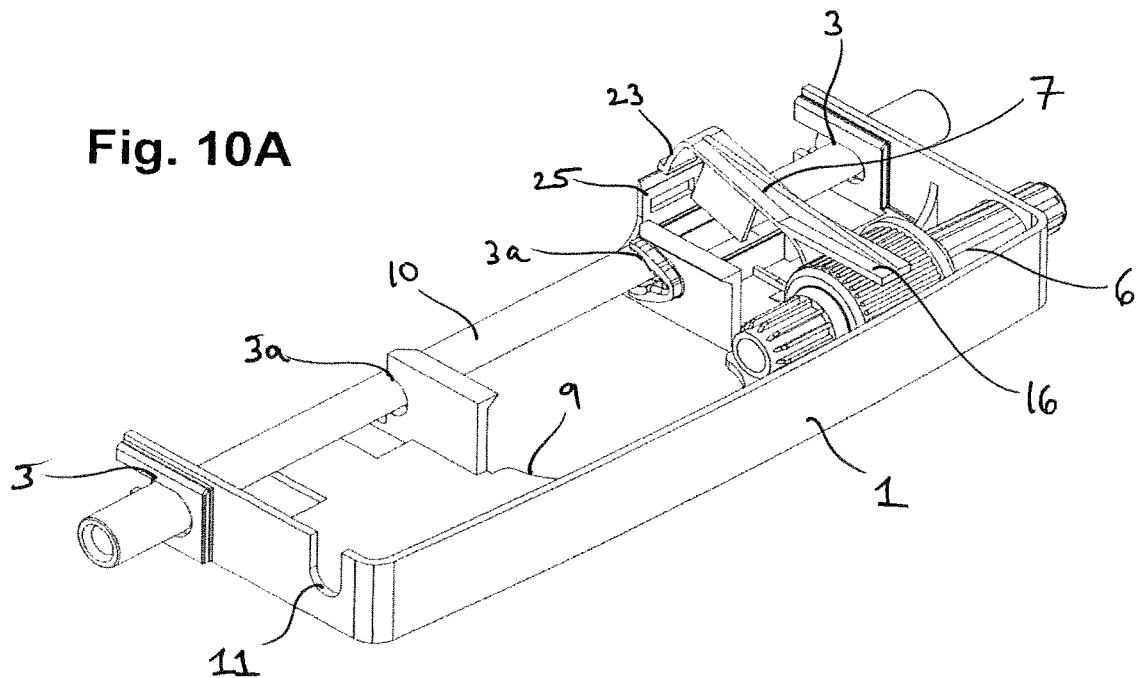
FIGS. 10A, 10B show perspective views of two preferred embodiments of the pinch clamp assembly according to the invention in their delivery status.
Figure 10B:
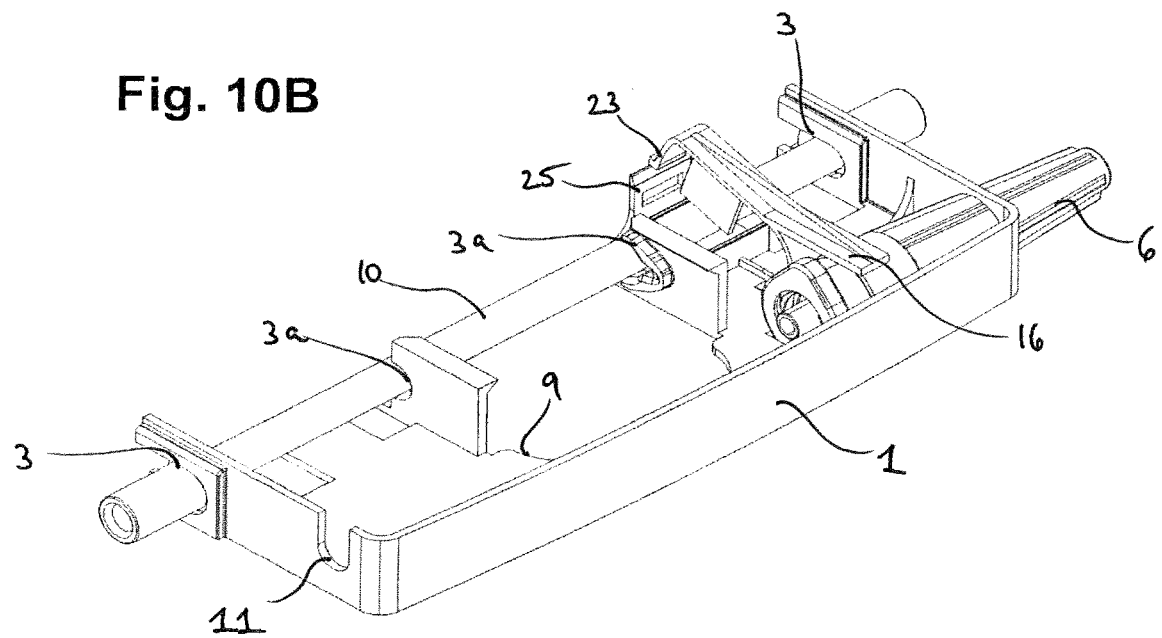

FIGS. 10A and 10B show perspective views of two preferred embodiments of the pinch clamp assembly according to the invention in the final delivery status after the clamping element 7 has been brought into its open position. The opening of the clamping element 7 is achieved by releasing the engagement between first locking means 23 and second locking means 25 of the clamping element 7 so as to open the area between the clamping surfaces and therefore to allow the silicon tube 10 to return to its relaxed sectional area. It is important to note, that in this delivery status of the pinch clamp assembly according to the invention the pumping section of silicon tube 10 is substantially not deformed in the sense that a sticking of the inner surfaces is avoided during storage of the pinch clamp assembly. However, in this delivery status there is no free flow situation of the pinch clamp assembly according to the invention because connector 6 is secured tightly within the assembly because retaining lever 16 of clamping element 7 exerts a force onto connector 6 so that it cannot be removed from the assembly without closing the clamping element 7. Therefore, it is not possible for medical personnel to attach the connector 6 to a port of a patient which would result in a free flow condition. It is the key principle of the present invention that while the retaining lever 16 which functions as a lock is exerting a force onto connector 6 in the open position of the clamping element 7, it is not possible to generate a free flow condition since the connector 6 is held tightly within the assembly and removing the connector 6 from the assembly is only possible after bringing the clamping element 7 to its closed position. Thus the flow through the pumping section of the silicon tube 10 is always occluded before inserting the pinch clamp assembly into the pump.

Bringing the pinch clamp assembly according to the invention from the status of FIGS. 9A and 9B to the status of FIGS. 10A and 10B requires that the engagement of first locking means 23 with second locking means 25 be released. This can be achieved by a release member 4, or an external tool, as part of the assembling process of the pinch clamp assembly according to the invention wherein this special tool pushes the second locking means 25 towards portion 21 of the clamping element 7 so as to release the hook-type engagement of the locking means, as shown by the arrows in FIGS. 9A and 9B. It is obvious that this releasing of the clamping element 7 cannot be accomplished easily, for example only with fingers. FIGS. 10A and 10B also show that the retaining lever 16 of clamping element 7 is tightly fitted over connector 6. Also, the retaining lever 16 extends over the most part of the surface of connector 6 making it impossible to take connector 6 out of the assembly in this status. As stated above, a lateral movement is prevented by the supporting means 5.

It is to be noted that the pinch clamp assembly as shown in FIGS. 10A and 10B cannot be mounted to an enteral feeding or infusion pump as is. Before the mounting can take place, connector 6 has to be removed. This is only possible after clamping element 7 has been brought into the closed position. It is clear that bringing the clamping element 7 into its closed position will also give open access to connector 6 which can be taken out of the assembly and connected to a port in order to set up the enteral feeding or infusion set. When mounting the pinch clamp assembly, with connector 6 removed, to the enteral feeding or infusion pump the clamping element 7 is still in its closed position thereby occluding the flow of liquid through the pumping section of silicon tube 10. The free flow condition is thus avoided. However, the occluded status of the pumping section of the silicon tube 10 must be released as soon as the cassette 1 with the other components of the pinch clamp assembly are mounted in the enteral feeding or infusion pump. The cassette shape of the base of the pinch clamp assembly facilitates the handling and the mounting of the assembly to the pump.

In the above preferred embodiment a locking and releasing mechanism has been described. It is to be noted, that other locking-releasing mechanisms are possible such as a magnetic solution or a solution with fastening means. All alternative solutions however should fulfil the central requirement which is that they are tamper-resistant so that the clamping element 7 cannot be opened easily by hand or with tools which are easily available to medical personnel.

With the subject-matter of the present invention a pinch clamp assembly for engaging a tube with an enteral feeding or an infusion pump adapted to feed nutritionals or to infuse medical solutions to a patient has been provided which comprises a relatively simply construction, ensures an anti-free-flow mechanism that works at all times, allows for a long time storage of the silicon tube, is uniform with regard to the used material in order to be easily recyclable and can be used with a number of enteral feeding or infusion pumps.

The invention claimed is:

1. A pinch clamp assembly for engaging a tube with a pump adapted to deliver solutions to a patient, the pinch clamp assembly comprising:
    a base comprising a holder for holding a pumping section of the tube in operative engagement with the base and a support for supporting a connector;
    a clamping element having clamping surfaces engageable with the pumping section and moveable between an open position allowing the flow of fluid through the pumping section and a closed position wherein the pumping section is occluded by the clamping element, and a first lock and a second lock adapted to engage with each other in the closed position and adapted to interact with a release member external to the pinch clamp assembly so as to bring the clamping element from the closed to the open position;
    a connector for connecting the tube with a port on a patient, the connector being removable from the pinch clamp assembly;
    the clamping element also comprising a retaining lever;
    in the open position of the clamping element the connector is retained by the retaining lever; and
    the clamping element is adapted to engage with the release member to release the clamping element to the open position when the pinch clamp assembly is mounted to the pump and the connector is removed.

2. The pinch clamp assembly of claim 1, wherein the base and the clamping element are integrally formed.

3. The pinch clamp assembly of claim 1, wherein the connector is selected from the group consisting of an enteral spike, an IV spike, an enteral feeding adapter, an IV luer lock adapter, and combinations thereof.

4. The pinch clamp assembly of claim 1, wherein the base is formed as a cassette such that the pinch clamp assembly may be integrally mounted to the pump.

5. The pinch clamp assembly of claim 1, wherein pinch clamp assembly made of recyclable plastic material and that the pumping section of the tube is made of silicon.

6. The pinch clamp assembly of claim 1, wherein the clamping element comprises a first leg with a tube blocking portion, a second leg with a flat surface, a bending portion acting as a spring element, the first lock at the free end of the first leg, the second lock at the free end of the second leg and the retaining lever is adjacent to the first leg and the bending portion, wherein the tube blocking portion and the flat surface may be pressed upon one another to squeeze the tube therebetween, and wherein the first and second locks are engageable with each other in the open position or in the closed position.

7. The pinch clamp assembly of claim 1, wherein the clamping surfaces have a characteristic selected from the group consisting of uneven, corrugated, finned, and combinations thereof.

8. The pinch clamp assembly of claim 1, wherein in the open position of the clamping element the retaining lever exerts a force on the connector so that the connector cannot be removed from the pinch clamp assembly.

9. The pinch clamp assembly of claim 1, wherein the connector is removable from the pinch clamp assembly only when the clamping element is in the closed position.

10. The pinch clamp assembly of claim 1, wherein the support comprises a first recess for accommodating the connector and a second recess for accommodating the tube associated with the connector.

11. A pump assembly comprising:

an enteral pump;

a pinch clamp assembly for engaging a tube with the enteral pump adapted to deliver solutions to a patient, the pinch clamp assembly comprising:

a base comprising a holder for holding a pumping section of the tube in operative engagement with the base and a support for supporting a connector, a clamping element having clamping surfaces engageable with the pumping section and moveable between an open position allowing flow of fluid through the pumping section and a closed position wherein the pumping section is occluded by the clamping element, and a first lock and a second lock adapted to engage with each other in the closed position and adapted to interact with a release member external to the pinch clamp assembly so as to bring the clamping element from the closed to the open position, and a connector for connecting the tube with a port on a patient, the connector being removable from the pinch clamp assembly, the clamping element also comprising a retaining lever, in the open position of the clamping element the connector is retained by the retaining lever, and the clamping element is adapted to engage with the release member to release the clamping element to the open position when the pinch clamp assembly is mounted to the pump and the connector is removed; and a releasing mechanism adapted to engage with the clamping element.

12. The enteral feeding pump of claim 11, wherein flow through the pumping section is only enabled when the pinch clamp assembly is mounted thereon.

13. A pump assembly comprising:

an infusion pump;

a pinch clamp assembly for engaging a tube with the infusion pump adapted to deliver solutions to a patient, the pinch clamp assembly comprising:

a base comprising a holder for holding a pumping section of the tube in operative engagement with the base and a support for supporting a connector, a clamping element having clamping surfaces engageable with the pumping section and moveable between an open position allowing flow of fluid through the pumping section and a closed position wherein the pumping section is occluded by the clamping element, and a first lock and a second lock adapted to engage with each other in the closed position and adapted to interact with a release member external to the pinch clamp assembly so as to bring the clamping element from the closed to the open position, a connector for connecting the tube with a port on a patient, the connector being removable from the pinch clamp assembly, the clamping element also comprising a retaining lever, in the open position of the clamping element the connector is retained by the retaining lever, and the clamping element is adapted to engage with the release member to release the clamping element to the open position when the pinch clamp assembly is mounted to the pump and the connector is removed; and a releasing mechanism adapted to engage with the clamping element.

14. The infusion pump of claim 13, wherein flow through the pumping section is only enabled when the pinch clamp assembly is mounted thereon.

* * * * *